United States Patent [19]

Beatty et al.

[11] Patent Number: 5,554,778
[45] Date of Patent: Sep. 10, 1996

[54] RUTHENIUM HYDROGENATION CATALYSTS

[75] Inventors: Richard P. Beatty, Newark, Del.; Rocco A. Paciello, Durkheim, Germany

[73] Assignee: E. I. Du Pont de Nemours and Company, Wilmington, Del.

[21] Appl. No.: 381,697

[22] Filed: Jan. 31, 1995

[51] Int. Cl.$^6$ .............................. C07F 15/00; C07F 9/02
[52] U.S. Cl. ................ 556/21; 556/22; 556/23; 556/136
[58] Field of Search ................ 556/22, 23, 21, 556/136

[56] References Cited

U.S. PATENT DOCUMENTS

| | | | |
|---|---|---|---|
| 3,454,644 | 7/1969 | Dewhirst | 260/570.9 |
| 4,362,671 | 12/1982 | Diamond et al. | 260/465.5 R |
| 4,482,760 | 11/1984 | Kleeman et al. | 568/811 |
| 4,810,825 | 3/1989 | Matsushita et al. | 568/840 |
| 5,151,543 | 9/1992 | Ziemecki | 558/459 |

OTHER PUBLICATIONS

Chaudret, B. et al., *Organometallics*, 4, 1722–1726 (1985).
Chaudret, B. et al, *J. Am. Chem. Soc.*, 113, 2314–2316 (1991).
Joshi, A. M. et al, *Prog. in Catal.*, 73, 143–146 (1992).
Arliguie, T. et al, *Organometallics*, 10, 1888 (1991).
Armit, P. W. et al, *J. Chem. Soc.*, Dalton Transactions, pp. 1663–1672 (1975).
Christ, M. L. et al, *Organometallics*, 13, 3800–3804 (1994).
Joshi, A. N. et al, *Inorg. Chim. Acta*, 198–200; 283–296 (1992).
Dehmlow, E. V., Universitat Bielefeld, Germany, *Kirk–Othmer Encyclopedia of Chem. Tech*, 4th Ed., 5, 374–383 (1993).
Grushin, V. V., *Acc. Chem. Res.*, 26, 279–286 (1993).
Albers, M. O. et al, *Inorganic Syntheses*, 26, 68–77 (1989).
Suarez, T. et al, *J. Mol. Cat.*, 45, 335 (1988).
Mizzoni, R. H. et al, *J. Med. Chem.*, 13(5), 878–882 (1970).
Yosida, T. et al, *JCS Chem. Commun.*, 870–871 (1979).

*Primary Examiner*—Porfirio Nazario-Gonzales

[57] ABSTRACT

The invention relates to a novel ruthenium complex having the formula Ru($\eta^3$-C$_6$H$_8$-PCy$_2$)(PCy$_3$)Cl, wherein Cy is cyclohexyl; its use in the preparation of RuHCl(H$_2$)(PCy$_3$)$_2$ and RuH$_2$(H$_2$)$_2$(PCy$_3$)$_2$; and the use of the complexes as catalysts in hydrogenation, imination and reductive hydrolysis processes.

14 Claims, 1 Drawing Sheet

RUTHENIUM HYDROGENATION CATALYSTS

FIELD OF THE INVENTION

This invention concerns a novel ruthenium complex, processes for the preparation of certain ruthenium complexes and processes for their use as catalysts in hydrogenation reactions.

TECHNICAL BACKGROUND

B. Chaudret and R. Poilblanc, *Organometallics*, 1985, 4, 1722–1726 report the synthesis and characterization of a ruthenium complex, $RuH_6(PCy_3)_2$. This complex was later formulated as $RuH_2(H_2)_2(PCy_3)_2$ by T. Arliguie et al., *Inorg. Chem.*, 1988, Vol. 27, 598–599. The complex was prepared from Ru(COD)(COT). (COD is 1,5-cyclooctadiene, COT is 1,3,5-cyclooctatriene and Cy is cyclohexyl.)

B. Chaudret et al., *J. Am. Chem. Soc.*, 1991, 113, 2314–2316, report the synthesis and characterization of a ruthenium complex $RuHX(H_2)(PCy_3)_2$, where X is iodine or chlorine. The complexes were prepared from $RuH_2(H_2)_2(PCy_3)_2$.

A. M. Joshi et al., *Prog in Catal.*, 1992, 73, 143 describes nitrile hydrogenations using di- and tri- nuclear Ru(II) complexes containing chelating diphosphines such as 1,4-bis(diphenylphosphino)butane (dppb). They disclose a preference for $[RuHCl(dppb)]_3$ for nitrile hydrogenations.

U.S. Pat. No. 3,454,644 describes hydrogenations using $L_nMZ_2$, where n=3 or 4; M is ruthenium or osmium; L is independently $PR_3$ or CO, preferably at least three being $PR_3$; and the Z ligands being Cl, Br, or H. Specifically mentioned are $RuHCl(PPh_3)_3$ and $RuH_2(PPh_2Me)_4$.

T. Arliguie et al., *Organometallics*, 1991, 10, 1888, disclose a structure for a compound in which dehydrogenation of a cyclohexyl ligand has apparently occurred. This structure is for a cationic (as opposed to neutral) species as indicated below.

X-ray crystallography shows that one cyclohexyl group has been dehydrogenated, with removal of two H atoms, to a cyclohexenyl group, which is coordinated to the Ru center as an olefin ligand and by an agostic C-H-Ru interaction involving one of the allylic hydrogens.

SUMMARY OF THE INVENTION

The present invention provides a neutral ruthenium complex, having the formula $Ru(\eta^3-C_6H_8-PCy_2)(PCy_3)Cl$, wherein Cy represents a cyclohexyl group, of the structure The present invention also provides a process for the preparation of a ruthenium complex having the formula $Ru(\eta^3-C_6H_8-PCy_2)(PCy_3)Cl$ wherein Cy is cyclohexyl comprising contacting a source of ruthenium, preferably cyclooctadienyl ruthenium dichloride, with tricyclohexylphosphine in the presence of a solvent; adding a base to the solution; and isolating the ruthenium complex from the solution.

This invention also provides a process for the preparation of a ruthenium complex having the formula $RuHCl(H_2)(PCy_3)_2$, wherein Cy is a cyclohexyl group comprising contacting a ruthenium complex having the formula $Ru(\eta^3-C_6H_8-PCy_2)(PCy_3)Cl$ with hydrogen in the presence of a solvent and agitating the solution to form $RuHCl(H_2)(PCy_3)_2$.

This invention further provides a process for the preparation of a ruthenium complex, having the formula $RuH_2(H_2)_2(PCy_3)_2$, wherein Cy is a cyclohexyl group, by contacting a ruthenium complex having the formula $Ru(\eta^3-C_6H_8-PCy_2)(PCy_3)Cl$ or $RuHCl(H_2)(PCy_3)_2$ with hydrogen in the presence of a strong base, water, an organic solvent and a phase transfer catalyst to form a biphasic medium and subsequently agitating the medium to form $RuH_2(H_2)_2(PCy_3)_2$.

This invention further provides a process for the hydrogenation of an organic nitrile, comprising contacting said nitrile with gaseous hydrogen in the presence of a ruthenium complex catalyst having the formula: $Ru(\eta^3-C_6H_8-PCy_2)(PCy_3)Cl$ or $RuHCl(H_2)(PCy_3)_2$, wherein Cy is a cyclohexyl group; and subsequently agitating the nitrile, hydrogen and catalyst to form a primary amine.

This invention also provides a process for the selective hydrogenation of a dinitrile, comprising the steps of contacting said dinitrile with gaseous hydrogen in the presence of a ruthenium complex catalyst having the formula $Ru(\eta^3-C_6H_8-PCy_2)(PCy_3)Cl$ or $RuHCl(H_2)(PCy_3)_2$, wherein Cy is a cyclohexyl group; and subsequently agitating the dinitrile, hydrogen and catalyst for an amount of time selected to favor yield of an aminonitrile over yield of a diamine.

This invention provides a process for the reductive hydrolysis of an organic nitrile, comprising the steps of contacting said nitrile with gaseous hydrogen and water in the presence of a ruthenium complex catalyst having the formula $Ru(\eta^3-C_6H_8-PCy_2)(PCy_3)Cl$ or $RuHCl(H_2)(PCy_3)_2$ wherein Cy is a cyclohexyl group; and subsequently agitating the nitrite, water, hydrogen and catalyst to form an alcohol.

This invention also provides a process for the selective reductive hydrolysis of a dinitrile, comprising the steps of contacting said dinitrile with gaseous hydrogen and water in the presence of a ruthenium complex catalyst having the formula $Ru(\eta^3-C_6H_8-PCy_2)(PCy_3)Cl$ or $RuHCl(H_2)(PCy_3)_2$, wherein Cy is a cyclohexyl group; and subsequently agitating the dinitrile, hydrogen, water and catalyst for an mount of time selected to favor yield of an hydroxynitrile over yield of a diol.

This invention further provides a process for the reductive imination of a nitrile to an aldimine, comprising the steps of contacting said nitrile with gaseous hydrogen and a primary amine in the presence of a ruthenium complex catalyst having the formula $Ru(\eta^3\text{-}C_6H_8\text{-}PCy_2)(PCy_3)Cl$ or $RuHCl(H_2)(PCy_3)_2$, wherein Cy is a cyclohexyl group; and subsequently agitating the nitrite, hydrogen, amine and catalyst to form said aldimine.

This invention also provides a process for the hydrogenation of an organic nitro compound to a primary amine, comprising the steps of contacting the nitro compound having at least one $NO_2$ group with gaseous hydrogen in the presence of a ruthenium complex catalyst having the formula $Ru(\eta^3\text{-}C_6H_8\text{-}PCy_2)(PCy_3)Cl$ or $RuHCl(H_2)(PCy_3)_2$, wherein Cy is a cyclohexyl group; and subsequently agitating the nitro compound, hydrogen and catalyst to form the primary amine.

DETAILED DESCRIPTION OF THE INVENTION

This invention provides a novel neutral ruthenium complex, $Ru(\eta^3\text{-}C_6H_8\text{-}PCy_2)(PCy_3)Cl$, wherein Cy represents a cyclohexyl group, which can be represented by the structure:

This complex can be prepared by a process represented by the equation:

where COD represents a 1,5-cyclooctadienyl group and Cy represents a cyclohexyl group. The base can be, for example, a Grignard reagent, for example, $Me_3SiCH_2MgCl$; or other base, for example, potassium-t-butoxide or sodium hydroxide. Preferably the base has a pKa greater than 13. Choice of base will be on the basis of availability, economics, or material compatibility with downstream processes such as product formation or waste treatment.

Although $(COD)RuCl_2$ is shown in the equation above, alternate sources of ruthenium can be used. Sources of ruthenium, for example, bis(alkene)ruthenium (II) compounds, comprise compounds of the formula $R^1_2RuX_2$, wherein $R^1$ represents an alkene ligand and X is a halide or a pseudohalogen (e.g., the anion of a protonic acid salt, such as nitrate or acetate). The alkene ligands are straight chain, branched, or cyclic arrangements of carbon atoms connected by single, double, or triple carbon-to-carbon bonds, comprising at least one carbon-to-carbon double bond, and substituted accordingly with hydrogen atoms. The alkene ligands can be present either as two separate ligands or as a single polyalkene ligand. Polyalkene ligands such as cycloheptatriene, norbornadiene, and 1,5-cyclooctadiene (COD) are preferred, with 1,5-cyclooctadiene being the most preferred. More complicated alkene ligands can be employed if desired, but offer no significant advantage over simple, inexpensive, alkene ligands. Examples of bis(alkene)ruthenium(II) compounds comprise (norbornadiene)$RuCl_2$, (cyclohexadiene)$RuCl_2$, and (cycloheptatriene)$RuCl_2$. The preferred bis(alkene)ruthenium(II) compounds are (1,5-cyclooctadiene)$RuX_2$ compounds with $(COD)RuCl_2$ being the most preferred. $(COD)RuCl_2$ can be prepared as described in M. O. Albers, et at., Inorganic Syntheses, 1989, 26, p. 68.

Preparation of $Ru(\eta^3\text{-}C_6H_8\text{-}PCy_2)(PCy_3)Cl$ is carried out in a solvent. Any solvent which is inert to the reactants and products can be employed. Aprotic solvents are preferred, commonly defined as those with autoprotolysis equilibrium constants less than about $10^{-20}$. (C. Reichardt, "Solvents and Solvent effects in Organic Chemistry, 2nd Edition", VCH Publishers (1968), especially pages 61–67). Ethers are especially preferred, such as dimethyl ether, diethyl ether, t-butyl methyl ether, tetrahydrofuran, and dioxane. The temperature for the present process ranges from about −78° C. to about 200° C., preferably about 0° C. to about 100° C., most preferably about 20° C. to about 40° C. under an inert atmosphere such as nitrogen, argon or helium. Pressure for this reaction is not an important variable; normal atmospheric pressure is usually employed.

The ruthenium complex, $Ru(\eta^3\text{-}C_6H_8\text{-}PCy_2)(PCy_3)Cl$ is prepared by contacting the source of ruthenium with the tricyclohexylphosphine and solvent and subsequently agitating the solution, usually by stirring. The base is then added to the solution with additional stirring. After an appropriate length of time, the solvent is removed and the ruthenium complex product isolated. The reaction is normally complete in about 12 to about 24 hours at 25° C., as indicated by the deep purple color of the complex product. The solvent is removed and the complex product dissolved in an aromatic hydrocarbon solvent. Suitable aromatic hydrocarbon solvents comprise $C_6$–$C_{12}$ non-fused benzenoid hydrocarbons and $C_1$–$C_{18}$ alkyl derivatives thereof. Examples of suitable solvents include benzene, toluene, ethylbenzene and xylene. The solution is filtered, the solvent removed from the filtrate, and the product washed with aliphatic hydrocarbon solvent to obtain the complex as a solid. Suitable aliphatic hydrocarbon solvents comprise $C_3$–$C_{12}$ linear or branched saturated aliphatic or alicyclic hydrocarbons, such as propane, butane, pentane, hexane, methylpentane, or mixtures of such hydrocarbons such as petroleum ether. The product complex is suitable for use as a catalyst without further purification.

The structure of the ruthenium complex $Ru(\eta^3\text{-}C_6H_8\text{-}PCy_2)(PCy_3)Cl$ has been determined on the basis of analytical and spectroscopic data. Gas chromatography established that the use of a 1,5-cyclooctadiene ligand results in a cyclooctene by-product, and that when trimethylsilylmethylmagnesium chloride is used as base, the trimethylsilylmethyl fragment ends up as tetramethylsilane.

Microanalysis and NMR data are consistent with a molecular formula for $Ru(\eta^3\text{-}C_6H_8\text{-}PCy_2)(PCy_3)Cl$ of $C_{36}H_{63}ClP_2Ru$. A cryoscopic molecular weight determination in benzene showed the complex to be monomeric with molecular weight of approximately 674 (vs 694 expected, well within experimental error). Fast Atom Bombardment (FAB) mass spec showed a grouping at mass 693$^+$. {M+H}$^+$ for Ru($\eta^3$-C$_6$H$_8$-PCy$_2$)(PCy$_3$)Cl should appear at 695, which is not observed. The 693$^+$ grouping probably arises from protonation of Ru($\eta^3$-C$_6$H$_8$-PCy$_2$)(PCy$_{3l}$)$_{Cl}$ (694→695$^+$) followed by rapid loss of H$_2$ (695$^+$→693$^+$). The 693$^+$ isotope pattern is as expected for C$_{36}$H$_{62}$ClP$_2$Ru.

The most distinctive feature of Ru($\eta^3$-C$_6$H$_8$-PCy$_2$)(PCy$_3$)Cl is its $^{31}$P NMR spectrum, which clearly shows two very different phosphine ligands with a very large P—P coupling constant, suggesting a trans arrangement. $^{13}$C NMR shows 9 methine carbons and 27 methylene carbons. The normal PCy$_3$ ligand, i.e., the ligand banded to the metal by a P-metal bond only, accounts for 15 of the methylenes and 3 of the methines. Further, 2 additional methines and 10 methylenes were attributed to two normal (un-metallated) cyclohexyl rings on the metallated phosphine ligand. The remaining 4 methines and 2 methylenes are attributed to a symmetrically bonded $\eta^3$-C$_6$H$_8$ ring.

The $\eta^3$-C$_6$H$_8$ feature resembles an $\eta^3$-allyl group, but the $^{13}$C shifts of the allyl carbons are significantly upfield of normal allyls. This may be due to non-optimal geometry imposed by the strongly constrained ring system. Alternatively, rather than being described as a symmetrical $\eta^3$-allyl, this complex might be described as an $\eta^1,\eta^2$-allyl (i.e., a σ complex with a π-bonded olefin), with rapid exchange to equilibrate the end carbons. An attempt to freeze such a process out using variable temperature NMR was unsuccessful down to −90° C. Proton, phosphorus, and carbon NMR, together with homonuclear and heteronuclear correlational NMR spectroscopy (proton-proton, proton-phosphorus, and proton-carbon COSY) which facilitated assignment of all observed NMR signals, provided strong support for the assigned structure. No evidence for a hydride ligand was seen even at low temperature.

Starting with Ru($\eta^3$-C$_6$H$_8$-PCy$_2$)(PCy$_3$)Cl, the present invention provides new processes for the synthesis of several ruthenium complexes, for example, RuHCl(H$_2$)(PCy$_3$)$_2$ and RuH$_2$(H$_2$)$_2$(PCy$_3$)$_2$, which were in the past only accessible by more complicated and unreliable routes.

Hydrogenation of the ruthenium complex Ru($\eta^3$-C$_6$H$_8$-PCy$_2$)(PCy$_3$)Cl of the present invention very cleanly produces as a product a ruthenium complex having the formula RuHCl(H$_2$)(PCy$_3$)$_2$. The same product is obtained by a process of the present invention through hydrogenation of Ru($\eta^3$-C$_6$H$_8$-PCy$_2$)(PCy$_3$)Cl in the presence of an amine base, for example, triethylamine or butylamine. The hydrogenation of either reaction is carried out in a solvent. Any solvent which is inert to the reactants and products can be employed. Preferred solvents comprise aromatic and aliphatic hydrocarbons, ethers, and amines. The volume of solvent must be sufficient to allow effective agitation, but it is not necessary for Ru($\eta^3$-C$_6$H$_8$-PCy$_2$)(PCy$_3$)Cl to be completely dissolved for satisfactory reaction to occur. Aliphatic or alicyclic hydrocarbons are especially preferred solvents, since they facilitate isolation of the product, which is essentially insoluble and can be easily isolated by filtration. By aliphatic or alicyclic hydrocarbons is meant any linear, branched, or cyclic arrangement of carbon atoms connected by single bonds only, with hydrogens attached as appropriate, for example, methane, ethane, propane, butane, pentane, hexane, heptane, octane, nonane, decane, undecane, dodecane, cyclopropane, cyclobutane, cyclopentane, cyclohexane, 2,3-dimethylbutane and methylcyclohexane. Further, mixtures of two or more such compounds can be used, for example, "petroleum ether" which is commonly sold by specifying a boiling range rather than an exact composition.

The hydrogenation is carried out under an atmosphere of hydrogen gas or any mixture of hydrogen gas with other gases that do not interfere with the desired reaction, such as N$_2$, He, Ne, or Ar. The partial pressure of hydrogen should be between about 100 kPa and about 1500 kPa. The preferred pressure is about 100 kPa to about 1000 kPa. Higher pressures can be used, but are not required and generally do not justify the expense of the more exotic equipment required.

Agitation is required, and can be provided by any convenient method, such as mechanical stirring or gas sparging. The method of agitation is unimportant as long as sufficient contact is provided for gaseous hydrogen to react with Ru($\eta^3$-C$_6$H$_8$-PCy$_2$)(PCy$_3$)Cl in solution or suspension.

The temperature range employed for this hydrogenation is about −80° to about 200° C. The preferred range is about 20° to about 60° C.

The hydrogenation product is not necessarily isolated before its own use as a catalyst. The RuHCl(H$_2$)(PCy$_3$)$_2$ prepared by this method is pure enough to be used without isolation or purification of any kind, either as a solution or suspension. Alternatively, if aliphatic hydrocarbon solvents are used as solvent, the product RuHCl(H$_2$)(PCy$_3$)$_2$ can be obtained as a solid precipitate which can be isolated by filtration.

Exposure of Ru(($\eta^3$-C$_6$H$_8$-PCy$_2$)(PCy$_3$)Cl to hydrogen rapidly hydrogenates the metallated PCy$_3$ ligand back to a normal PCy$_3$ ligand. This is supported by both $^{31}$P and $^{13}$C nmr, which shows only resonances expected for two equivalent normal PCy$_3$ ligands in the hydrogenated product.

The present invention further provides a process whereby upon hydrogenation of a ruthenium complex having the formula Ru($\eta^3$-C$_6$H$_8$-PCy$_2$)(PCy$_3$)Cl or RuHCl(H$_2$)(PCy$_3$)$_2$ in the presence of water, a strong base and a phase-transfer catalyst, a ruthenium complex having the formula RuH$_2$(H$_2$)$_2$(PCy$_3$)$_2$ is produced. This reaction can be conducted in biphasic media, comprising a strongly basic aqueous phase and an organic phase which comprises the ruthenium starting material.

The organic solvent should be immiscible with the aqueous phase and unreactive toward the starting materials and products. Aprotic solvents, commonly defined as those with autoprotolysis equilibrium constants less than about 10$^{-20}$, are preferred. Hydrocarbon solvents, such as benzene or toluene, are especially preferred.

A base is added to the aqueous phase to maintain pH >12. The base can be either organic or inorganic, but it must be soluble in the aqueous phase and not have an appreciable solubility in the organic phase. Other than maintaining a high enough pH for the reaction to occur, the only other requirement for the base is that it not participate in undesired reactions with other reactants or solvents. The preferred bases are the Group I or II hydroxides, for example, LiOH, NaOH, KOH, and Ca(OH)$_2$, with NaOH being most preferred. Stronger bases can be used if desired, but because of their leveling effect in water, these bases will function equivalently to hydroxide. For example, sodium hydride is a much stronger base than sodium hydroxide, but in water it is instantly converted to hydrogen and sodium hydroxide.

The success of the present process depends on reaction of the aqueous base with the ruthenium compound present in the organic solvent. Aqueous alkali metal hydroxides (e.g., NaOH) have essentially no solubility in organic media and the ruthenium reactants have essentially no solubility in the aqueous caustic phase, therefore the desired reaction does not occur at an acceptable rate in the absence of a phase transfer catalyst (PTC).

One broad class of phase transfer catalyst useful in the present process can be represented as $Q^+Y^-$, where $Q^+$ represents a cation and $Y^-$ an anion. This type of phase transfer catalyst includes, for example, quaternary ammonium halides (e.g., benzyl triethyl ammonium chloride, tetrabutyl ammonium bromide) and tetraalkyl phosphonium halides (e.g., tetrabutyl phosphonium chloride). Another broad class of phase transfer catalyst includes linear and cyclic polyethers or polyether amines (e.g., polyalkylene glycols, Crown ethers, and Cryptands such as Kryptofix 222®, a product of E. M. Science, Gibbstown, N.J.). Any of these phase transfer catalysts are suitable in the present process provided that they do not participate in undesired reactions with solvents or other reactants. A preferred phase transfer catalyst is benzyltriethylammonium chloride since it is relatively inexpensive, widely used and readily available.

Phase transfer catalysts are believed to function by forming ion pairs which have higher solubility in the organic phase of the two-phase reaction than the ion pairs present in the absence of the phase transfer catalyst. For example, NaOH has very low solubility in organic media. In the presence of a quaternary salt phase transfer catalyst ($Q^+Y^-$), ion pairs such as $Q^+OH^-$ can form which have higher solubility in the organic phase, greatly enhancing reaction rate. In essence, the phase transfer catalyst acts to transport the reactive anion to the organic phase, where it can participate in the desired reaction. Crown ethers, Cryptands, polyalkalene glycols, and other neutral phase transfer catalysts are believed to function by complexing or encapsulating the aqueous cation, again forming an ion pair with enhanced organic solubility (e.g., K●Crown ether$^+$OH$^-$), which can be transported into the organic phase for reaction. In the organic phase, the ruthenium compound is thought to first react with phosphine ligands and hydrogen to generate reactive intermediates containing dihydrogen or hydride ligands as well as X ligands. Hydroxide anion, transported into the organic phase by the phase transfer catalyst as $Q^+OH^-$, is thought to react with these intermediate ruthenium species by abstracting $H^+X^-$, forming water, a new ruthenium species, and a new ion pair $Q^+X^-$. The exact mechanism by which this occurs is unknown, and is not important to successful application of this method. $Q^+X^-$ then migrates back to the aqueous phase, releasing $X^-$ and picking up another $OH^-$ to repeat the cycle.

The phase transfer catalyst is used in catalytic amounts. The preferred amount of phase transfer catalyst is about 1% to about 10% on a molar basis compared to the amount of ruthenium used. Smaller amounts of phase transfer catalyst can be used, but require longer reaction times. Larger amounts can also be used, but result in increased cost.

The source of hydrogen comprises hydrogen gas or a mixture of hydrogen gas with inert gases such as $N_2$, He, Ne, or Ar. Pure gaseous hydrogen is preferred. Mixtures comprising carbon monoxide, such as "synthesis gas" are not acceptable, since CO reacts with the desired ruthenium complexes to produce carbonyl complexes.

Because of the biphasic medium, effective agitation is required in order to provide sufficient contact of the gaseous hydrogen with $Ru(\eta^3-C_6H_8-PCy_2)(PCy_3)Cl$ or $RuHCl(H_2)(PCy_3)_2$ for the hydrogenation reaction to occur and to provide sufficient contact of the aqueous and organic phases for the phase transfer catalyst to function.

The temperature range employed is from about −30° C. (approximate freezing point of aqueous NaOH) to about 200° C. The preferred range is about 20° C. to about 100° C.

The partial pressure of hydrogen should be between about 100 kPa and about 15000 kPa. The preferred pressure is from about 700 kPa to about 7000 kPa. Higher pressures can be used, but are not required and generally do not justify the expense of the more exotic equipment required. The organic phase comprising the ruthenium complex, $RuH_2(H_2)_2(PCy_3)_2$, can be separated from the aqueous phase by decantation. The aqueous phase can be extracted with additional portions of solvent to increase recovery of $RuH_2(H_2)_2(PCy_3)_2$ from the aqueous phase. The resulting organic phase comprising $RuH_2(H_2)_2(PCy_3)_2$ can then be optionally washed with water to improve removal of residual base. The resulting organic phase comprising $RuH_2(H_2)_2(PCy_3)_2$ is generally used as a catalyst without further treatment. If desired, the $RuH_2(H_2)_2(PCy_3)_2$ can be isolated by one of the variety of methods known to those skilled in the art, such as evaporation of solvent, crystallization by cooling, or precipitation by addition of a second organic solvent which is a poor solvent for $RuH_2(H_2)_2(PCy_3)_2$. The exact isolation procedure depends on the amount and nature of the organic solvent used in the preparation. It is desirable to maintain a hydrogen atmosphere as much as possible during manipulation and isolation of $RuH_2(H_2)_2(PCy_3)_2$ to avoid loss of hydrogen from $RuH_2(H_2)_2(PCy_3)_2$.

Nitrile and nitro groups have been very difficult to hydrogenate using existing catalysts. The ruthenium complexes of the formula $Ru(\eta^3-C_6H_8-PCy_2)(PCy_3)Cl$ and $RuHCl(H_2)(PCy_3)_2$ are shown in the present invention to have utility as catalysts for hydrogenating nitriles and nitro compounds to primary amines under very mild conditions. For example, adiponitrile can be hydrogenated to hexamethylenediamine, a key monomer for nylon-6,6 using these ruthenium complexes.

Suitable nitrite substrates which are applicable in this hydrogenation process of the present invention comprise those having at least one CN group which is capable of being hydrogenated to the corresponding primary amine. Typically, the nitrite substrate is a monomeric material with one or two CN groups. However, the nitrile substrate can also be oligo- or polymeric, with either regularly occurring or occasional CN functional groups, comprising, for example, fluoronitriles such as $F(CF_2CF_2)_nCH_2CH_2CN$ wherein n ranges from 2 to about 6. Complete reduction of a dinitrile to a diamine is one embodiment of the present hydrogenation process.

Suitable nitrite substrates comprise the classes of linear or branched saturated aliphatic $C_2-C_{18}$ mono- and $C_3-C_{19}$ dinitriles and phenyl derivatives thereof, $C_4-C_{13}$ saturated alicyclic mono- and $C_5-C_{14}$ dinitriles, $C_3-C_{18}$ linear or branched olefinically unsaturated aliphatic nitriles, $C_6-C_{13}$ olefinically unsaturated alicyclic nitriles, $C_7-C_{14}$ aromatic mono- and dinitriles, $C_6-C_8$ heterocyclic nitrogen and oxygen mononitriles, $C_3-C_4$ cyanoalkanoic amides, $C_2-C_{12}$ saturated aliphatic cyanohydrins or hydroxynitriles, or mixtures of the above-described nitriles, wherein said nitriles can also contain non-interfering substituents.

Examples of some substituents which generally do not interfere with the desired hydrogenation reaction comprise hydroxyl, amine, ether, alkyl, alkoxy, and aryloxy. For example, cyanohydrins and hydroxynitriles are both acceptable nitriles. Unsaturated, hydrogenatable substituents such as aldehyde, ester, amide, imine, nitro, alkene, and alkyne are permissible in that they do not interfere with hydrogenation of the nitrile group, but they may themselves be hydrogenated partly or completely in the course of the nitrile hydrogenation. For example, 2-pentenenitrile can be hydrogenated completely to aminopentane. Carboxylic acids are generally not acceptable substituents since they react with the catalyst, deactivating it.

Representative examples of specific nitriles applicable in the invention process comprise: acetonitrile ($C_2$), propionitrile ($C_3$), butyronitrile ($C_4$), valeronitrile ($C_5$), capronitrile ($C_6$), 2,2-dimethylpropanenitrile, enanthonitrile ($C_7$), caprylonitrile ($C_8$), pelargononitrile ($C_9$), caprinitrile ($C_{10}$), hendecanenitrile ($C_{11}$), lauronitrile ($C_{12}$), tridecanenitrile ($C_{13}$), myristonitrile ($C_{14}$), pentadecanenitrile ($C_{15}$), palmitonitrile ($C_{16}$), margaronitrile ($C_{17}$), stearonitrile ($C_{18}$), phenylacetonitrile (benzyl nitrile), napthylacetonitrile, malononitrile, succinonitrile, glutaronitrile, 2-methylglutaronitrile, adiponitrile, acrylonitrile, methacrylonitrile, 2-methyleneglutaronitrile, 1,4-dicyano-2-butene, 1,4-dicyano-1-butene, dodecanedinitrile, 3-butenenitrile, 4-pentenenitrile, 3-pentenenitrile, 2-pentenenitrile, 2-hexenenitrile, 2-heptenenitrile, glycolonitrile (formaldehyde cyanohydrin), hydracrylonitrile (ethylene cyanohydrin), eqicyanohydrin (gamma-cyanopropylene oxide), lactonitrile, pyruvonitrile, cyclohexanecarbonitrile, cyclododecanecarbonitrile, benzonitrile, o-tolylnitrile, m-tolylnitrile, p-tolylnitrile, anthranilonitrile, m-aminobenzonitrile, p-aminobenzonitrile, 1-napthonitrile, 2-napthonitrile, phthalonitrile, isophthalonitrile, terephthalonitrile, mandelonitrile, 2-pyridinenitrile, 3-pyridinenitrile, 4-pyridinenitrile, or 2-furylacetonitrile.

Preferred nitriles in the process are adiponitrile, 2-methylglutaronitrile, and dodecanedinitrile.

The process can be conducted in the neat state, i.e., no solvent, provided that the nitrile and product amine are liquids at the reaction temperature employed and that the catalyst is sufficiently soluble therein. However, use of a solvent is preferred to facilitate contacting of the reactants and removal of heat. The solubility of the respective materials in the solvent (or mixture of solvents) should be significantly large enough to initiate and maintain the hydrogenation process.

Solvents which are applicable in the invention process must be inert toward hydrogenation under the reaction conditions and possess adequate solvating ability for the substrate nitrite and catalyst.

Although the solvent employed is normally and preferably anhydrous, this is not a strict requirement. While the amount of water present is normally, and preferably, less than about 0.01 mole of water per mole of nitrite, larger amounts of water, up to about 0.1 to about 1 mole of water per mole of nitrile, generally do not produce significant amounts of alcohol by-products. In the case of a hydrophobic nitrite and hydrophobic solvent, large amounts of water, even a second liquid phase, can be present and do not interfere with normal hydrogenation. Suitable solvents comprise $C_6$–$C_{12}$ non-fused benzenoid hydrocarbons and $C_1$–$C_{18}$ alkyl derivatives thereof, $C_5$–$C_{30}$ linear or branched saturated aliphatic or alicyclic hydrocarbons, $C_2$–$C_{12}$ aliphatic ethers, $C_4$–$C_{12}$ saturated aliphatic, alicyclic or cyclic mono- or diethers, or $C_7$–$C_{14}$ aromatic ethers, or mixtures thereof. By the term "non-fused benzenoid hydrocarbons" is meant that if more than one benzene ring is present in the hydrocarbon, the rings are isolated and not fused together. Thus, the term encompasses biphenyl, but not naphthalene.

Suitable solvents further comprise amines, especially those amines produced by hydrogenation of the above nitriles which are liquid at reaction temperature. Representative examples of specific useful solvents are ammonia, methylamine, ethylamine, n-propylamine, isopropylamine, n-butylamine, amylamine, azacycloheptane, 2-methyl-pentamethylenediamine and hexamethylenediamine, xylene, hexamethylbenzene, biphenyl, n-octadecylbenzene, benzene, toluene, pentane, cyclopentane, cyclohexane, methylcyclohexane, hexane, isooctane, decane, cyclodecane, tetrahydrofuran, p-dioxane, 2,5-dimethyltetrahydrofuran, methyl tetrahydrofurfuryl ether, dimethyl ether, 1,2-dimethoxyethane, diglyme, diethylether, diisopropyl ether, anisole, diphenylether, and mixtures thereof.

Preferred solvents comprise ammonia, THF, t-butyl methyl ether, toluene, n-amylamine, n-butylamine, 2-methyl-pentamethylenediamine, and hexamethylenediamine. Most preferred, when the amine product of the hydrogenation is a liquid at reaction temperature, is to use that same amine product as the reaction solvent. For example, butylamine can be used as the solvent when hydrogenating butyronitrile or hexamethylenediamine can be used as the solvent when hydrogenating adiponitrile.

The catalyst for this process of the present invention is selected from one of the complexes described herein, namely $Ru(\eta^3\text{-}C_6H_8\text{-}PCy_2)(PCy_3)Cl$ and $RuHCl(H_2)(PCy_3)_2$, wherein Cy is a cyclohexyl group. The amount of catalyst used can vary from about 10 mole percent, based on nitrile to be hydrogenated, to about 0.01 mole percent. The preferred amount of catalyst is between about 1% and about 0.1% of the amount of nitrile to be hydrogenated on a molar basis. Larger or smaller amounts of catalyst can be used at the expense of catalyst cost or reaction time respectively.

Excess tricyclohexylphosphine can be present if desired and does not interfere with hydrogenation. Although excess tricyclohexylphosphine is not required, the presence of excess tricyclohexylphosphine ensures that there is always adequate tricyclohexylphosphine to stabilize the ruthenium catalyst, even if adventitious oxygen oxidizes a small amount of tricyclohexylphosphine to tricyclohexylphospine oxide or other side reactions degrade portions of the tricyclohexylphosphine ligand. Tricyclohexylphosphine oxide formed in this manner can also be present and does not interfere with hydrogenation reactions. The molar ratio of excess tricyclohexylphosphine to ruthenium can vary from zero to about 60 or more. The preferred molar ratio is between zero and about 30, with a molar ratio of about 2 to about 25 being most preferred.

The hydrogenation can be conducted at any convenient temperature, from about 0° C. to about 200° C. Lower temperatures require prolonged reaction times while higher temperatures reduce catalyst life and reduce the yield of the desired primary amine products. The preferred temperature is in the range of about 60° C. to about 120° C., with about 80° C. to about 100° C. being most preferred.

The source of hydrogen comprises hydrogen gas or mixtures of hydrogen gas with other gases which do not interfere with the desired hydrogenation. Non-interfering gases comprise, for example, inert gases, such as helium, argon, and nitrogen. Oxygen and carbon monoxide should be avoided since they can react with the catalysts.

The pressure employed can be from about 100 kPa (1 atmosphere) to about 3550 kPa. Elevated pressures are preferred since the solubility of hydrogen is increased which leads to higher reaction rates. However, pressures above 7000 kPa are generally avoided due to the high cost of equipment capable of operating at such pressures. Pressures above about 4000 kPa can result in significant formation of aldimines rather than primary amines, as described below. The preferred pressure for production of primary ambles in high yield is therefore in the range from about 800 kPa to about 3550 kPa. Pressures between about 800 kPa and about 2000 kPa are most preferred. The exact preferred pressure depends to some extent on the substrate, solvent, concentration, and other experimental variables. Higher pressures can be employed if desired to increase reaction rate, but the yield of primary amine may be reduced with some substrates due to formation of aldimines. In such cases, aldimine byproducts can be reduced to some extent by lowering the concentration of the substrate and conducting the hydrogenation in a non-amine solvent, which is not capable of reacting to form aldimines. Suitable solvents comprise the aromatic and aliphatic hydrocarbons and ethers described above.

The complexes of the formula $Ru(\eta^3-C_6H_8-PCy_2)(PCy_3)Cl$ and $RuHCl(H_2)(PCy_3)_2$ are also useful as catalysts for hydrogenation of organic nitro groups to primary amine groups. For example, nitrobenzene can be hydrogenated to aniline. Use of the homogeneous catalysts of the present invention in place of traditional heterogeneous catalysts for nitro group hydrogenation can facilitate heat removal from these highly exothermic hydrogenation reactions and help maintain a uniform reaction temperature, thereby improving yield of the desired primary amine.

Nitro compounds which are applicable to the present invention are those having at least one $NO_2$ group which is capable of being hydrogenated to the corresponding primary amine. Multiple nitro groups can be present. Such nitro compounds can be represented by the formula $R'NO_2$, where $R'$ is a $C_1-C_{18}$ arrangement of carbon atoms in a linear, branched, or cyclic structure connected by single, multiple or aromatic bonds, with hydrogen atoms or other non-interfering substituents incorporated as appropriate. Examples of some substituents which generally do not interfere with the desired hydrogenation comprise alkyl, aryl, hydroxyl, amine, ether, alkoxy, and aryloxy. Unsaturated hydrogenatable substituents such as cyano, ketone, aldehyde, ester, amide, alkene and alkyne are permissable in that they do not interfere with hydrogenation of the nitro group, but they may themselves by hydrogenated partly or completely in the course of the nitro group hydrogenation.

The amount of catalyst, excess tricyclohexylphosphine, temperature, solvents, agitation requirements, and sources of hydrogen are as described above for hydrogenation of nitriles to amines. Pressure can range from about 100 kPa to about 15000 kPa. The preferred pressure is from about 700 kPa to about 7000 kPa.

The hydrogenation of nitriles and nitro compounds of the present invention is a two-phase reaction. Therefore, it is essential to provide adequate gas-liquid contact to enable the gaseous hydrogen to dissolve in the liquid reaction phase. Adequate gas-liquid contact can be facilitated by any of the various agitation methods familiar to those skilled in the art. Typical methods comprise sparging gas below the liquid surface in a tank reactor, stirring the liquid in a tank reactor to draw gas into the liquid and create bubbles, use of packing in a tower reactor to obtain high liquid surface area, or use of a bubble column reactor, wherein bubbles of gas are introduced into the reactor and rise through the liquid phase.

The present invention further provides a selective reduction process wherein a dinitrile is partially hydrogenated to yield an aminonitrile by using a ruthenium complex having the formula $Ru(\eta^3-C_6H_8-PCy_3)Cl$ or $RuHCl(H_2)(PCy_3)_2$ as a catalyst. For example, the major intermediate in adiponitrile hydrogenation, 6-aminocapronitrile, can be prepared in high yield if the hydrogenation is stopped at an intermediate stage. This aminonitrile can then be directly hydrolyzed and polymerized to nylon 6.

The dinitrile of the present process can be any aliphatic dinitrile comprising about 3 to about 19 carbon atoms, but preferably comprising about 6 to about 12 carbon atoms. Preferably, the carbon atoms are arranged in a linear or branched chain. Especially preferred examples of dinitriles and their products comprise adiponitrile hydrogenated to 6-aminocapronitrile, 2-methylglutaronitrile hydrogenated to a mixture of two isomeric aminonitriles (5-amino-2-methyl valeronitrile and 5-amino-4-methyl valeronitrile), and dodecanedinitrile hydrogenated to 12-aminododecanenitrile.

The amount of catalyst, excess tricyclohexylphosphine, solvents, temperature, pressure, agitation requirements and sources of hydrogen are the same as discussed above for the hydrogenation of nitriles to primary amines.

Figure 1:
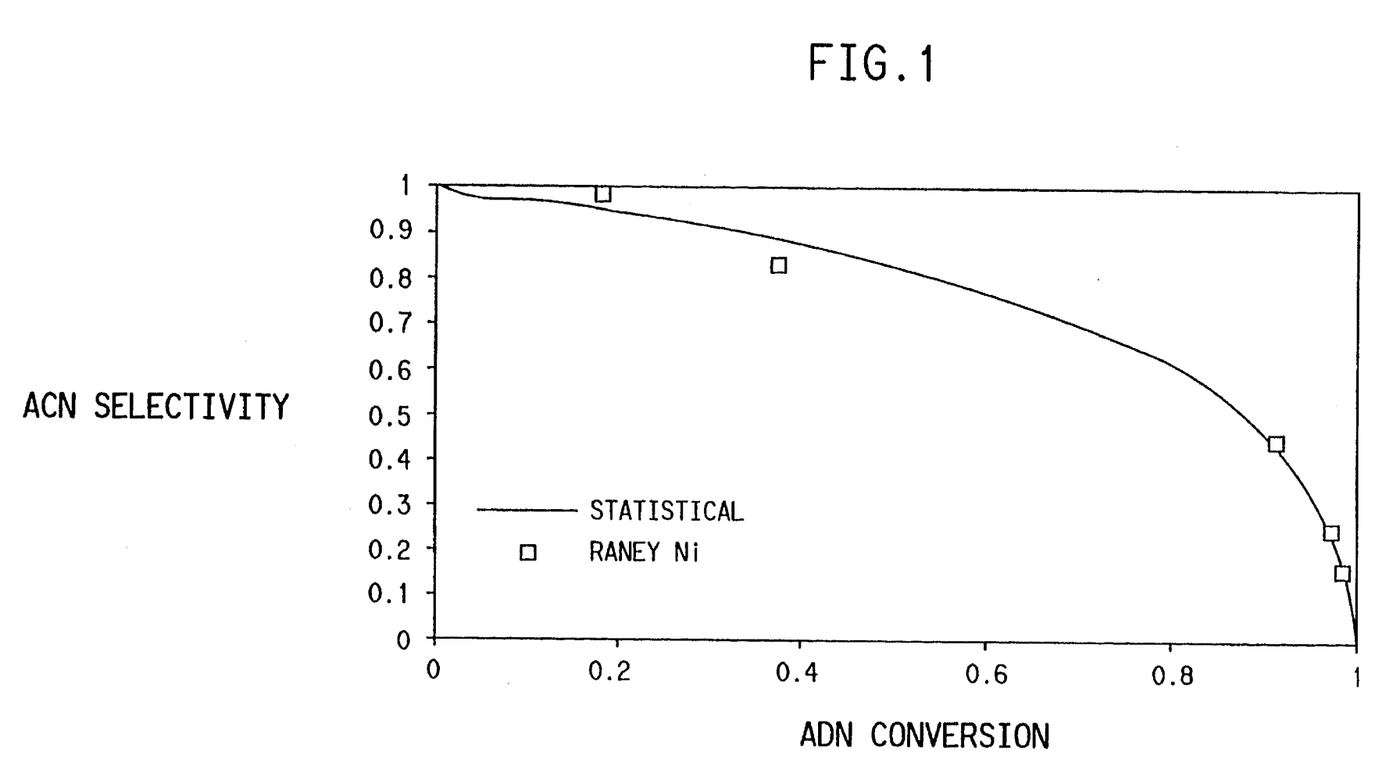
FIG. 1 is a graph showing the aminocapronitrile (ACN) selectivity calculated for an adiponitrile (ADN) hydrogenation where the two ends of the ADN are assumed to react independently and at the same rate (statistical selectivity) compared to the ACN selectivity actually obtained with a conventional unpromoted Raney Ni catalyst.

The desired product of the selective reduction, an aminonitrile, is an intermediate in one embodiment of the present hydrogenation process which eventually results in the formation of a diamine. The aminonitrile concentration in the reacting mixture passes through a maximum as the reaction progresses. One objective of this embodiment of the present invention is to maximize the concentration of the aminonitrile in the reacting mixture at the highest possible conversion of the starting nitrile. The yield of the aminonitrile and the position of the maximum with respect to dinitrile conversion depend on operating conditions such as temperature, hydrogen pressure, amount and kind of catalyst, dilution of starting dinitrile, as well as, the type of solvent. These variables in turn influence the optimum contact time for the reaction. Conventional nitrile hydrogenation catalysts such as Raney Ni frequently give aminocapronitrile (ACN) selectivities approximating those expected statistically, assuming the two ends of the dinitrile are hydrogenated independently and at comparable rates. FIG. 1 shows the calculated statistical ACN selectivity along with the selectivity actually obtained using an unpromoted Raney Ni catalyst (Raney Ni 2800, available commercially from W. R. Grace and Co., Baltimore, Md.). In contrast, the catalysts of the present invention give aminonitrile selectivities higher than those expected statistically.

The optimum reaction time of the present invention needed to favor formation of an aminonitrile need be determined only once for any given set of reaction conditions. Once the optimum has been determined, it will remain constant as long as reaction conditions, such as catalyst, temperature, concentrations and pressure are held constant. The contact time in the present selective reduction process is therefore selected to favor yield of aminonitrile over yield of a diamine.

The complexes $Ru(\eta^3-C_6H_8-PCy_2)-(PCy_3)Cl$ and $RuHCl(H_2)(PCy_3)_2$ are also useful as catalysts in the reductive hydrolysis of an organic nitrite to an alcohol. Significantly, dinitriles can be cleanly converted to diols using a process of the present invention. Reductive hydrolyses using the catalysts and process of the present invention have been found to be exceptionally clean and specific. The use of $RuHCl(H_2)(PCy_3)_2$ is preferred, although $Ru(\eta^3-C_6H_8-PCy_2)(PCy_3)Cl$ is easily used as an alternate catalyst since it has been shown by the present invention to quantitatively convert to $RuHCl(H_2)(PCy_3)_2$ on exposure to hydrogen.

Nitrite substrates which are applicable in the reductive hydrolysis process of the present invention are those which comprise at least one CN group capable of being reductively hydrolyzed to the corresponding primary alcohol. Typically, the nitrite substrate is a monomeric material with one or two CN groups. However, the substrate can also be oligo- or polymeric, with either regularly occurring or occasional CN functional groups, comprising, for example, fluoronitriles such as, $F(CF_2CF_2)_nCH_2CH_2CN$, wherein n ranges from 2 to about 6. Complete reductive hydrolysis of a dinitrile to a diol is one embodiment of the present reductive hydrolysis process.

Suitable substrates comprise the classes of linear or branched saturated aliphatic $C_2$–$C_{18}$ mono- and $C_3$–$C_{19}$ dinitriles and phenyl derivatives thereof, $C_4$–$C_{13}$ saturated alicyclic mono- and $C_5$–$C_{14}$ dinitriles, $C_3$–$C_{18}$ linear or branched olefinically unsaturated aliphatic nitriles, $C_6$–$C_{13}$ olefinically unsaturated alicyclic nitriles, $C_7$–$C_{14}$ aromatic mono- and dinitriles, $C_6$–$C_8$ heterocyclic nitrogen and oxygen mononitriles, $C_3$–$C_4$ cyanoalkanoic amides, $C_2$–$C_{12}$ saturated aliphatic cyanohydrins or hydroxynitriles, or mixtures of the above-described nitriles, wherein said nitriles can also contain non-interfering substituents.

Examples of some substituents which generally do not interfere with the desired reduction reaction comprise hydroxyl, amine, ether, alkyl, alkoxy, and aryloxy. For example, cyanohydrins and hydroxynitriles are both acceptable nitriles. Unsaturated, hydrogenatable substituents such as aldehyde, ester, amide, imine, nitro, alkene, and alkyne are permissible in that they do not interfere with reductive hydrolysis of the nitrile group, but they may themselves be hydrogenated partly or completely in the course of the nitrile hydrogenation. For example, 2-pentenenitrile can be reductively hydrolyzed completely to 1-pentanol. Carboxylic acids are generally not acceptable substituents since they react with the catalyst, deactivating it.

Representative examples of specific nitriles applicable in the invention process are: acetonitrile ($C_2$), propionitrile ($C_3$), butyronitrile ($C_4$), valeronitrile ($C_5$), capronitrile ($C_6$), 2,2-dimethylpropanenitrile, enanthonitrile ($C_7$), caprylonitrile ($C_8$), pelargononitrile ($C_9$), caprinitrile ($C_{10}$), hendecanenitrile ($C_{11}$), lauronitrile ($C_{12}$), tridecanenitrile ($C_{13}$), myristonitrile ($C_{14}$), pentadecanenitrile ($C_{15}$), palmitonitrile ($C_{16}$), margaronitrile ($C_{17}$), stearonitrile ($C_{18}$), phenylacetonitrile (benzyl nitrite), napthylacetonitrile, malononitrile, succinonitrile, glutaronitrile, 2-methylglutaronitrile, adiponitrile, acrylonitrile, methacrylonitrile, 2-methyleneglutaronitrile, 1,4-dicyano-2-butene, 1,4-dicyano-1-butene, dodecanedinitrile, 3-butenenitrile, 4-pentenenitrile, 3-pentenenitrile, 2-pentenenitrile, 2-hexenenitrile, 2-heptenenitrile, glycolonitrile (formaldehyde cyanohydrin), hydracrylonitrile (ethylene cyanohydrin), eqicyanohydrin (gamma-cyanopropylene oxide), lactonitrile, pyruvonitrile, cyclohexanecarbonitrile, cyclododecanecarbonitrile, benzonitrile, o-tolylnitrile, m-tolylnitrile, p-tolylnitrile, anthranilonitrile, m-aminobenzonitrile, p-aminobenzonitrile, 1-napthonitrile, 2-napthonitrile, phthalonitrile, isophthalonitrile, terephthalonitrile, mandelonitrile, 2-pyridinenitrile, 3-pyridinenitrile, 4-pyridinenitrile, or 2-furylacetonitrile.

Preferred nitriles in the process are adiponitrile, 2-methylglutaronitrile, and dodecanedinitrile. Also preferred is 3-cyano methyl isobutyrate which cyclizes on reductive hydrolysis producing 2-methyl-butyrolactone, which can be hydrogenated using conventional technology to 3-methyltetrahydrofuran, a useful monomer for polyalkalene glycols.

Water is a required reactant in the reductive hydrolysis. At least one mole of water is required per mole of nitrite, but larger amounts are typically used, and quantities of 2000 moles water per mole nitrile or even more can be used. The preferred amount of water is about 30 to about 300 moles water/mole nitrile. Larger amounts of water enhance selectivity to alcohols but make product isolation more difficult. Smaller amounts of water reduce the selectivity to alcohols, increasing the amount of amines produced.

In general the same classes of solvents as described above for nitrile hydrogenation are suitable. However, it is essential that adequate water be available to the reacting nitrile to achieve the desired reductive hydrolysis, producing alcohol, rather than simple hydrogenation which would produce amine. There are three possible modes of operation: (a) neat, i.e., without any solvent other than starting nitrile or product alcohol, (b) with a water immiscible solvent, or (c) with a homogenizing solvent.

The preferred mode of operation depends on the nature of the nitrile being reacted, keeping in mind the necessity of providing adequate water for reductive hydrolysis to occur rather than simple reduction. The main criterion is the ability of the nitrile or product alcohol to dissolve the reactants (nitrile, catalyst, and water) sufficiently to enable reductive hydrolysis to occur.

"Hydrophilic" and some "amphiphilic" nitrile reactants, those which are liquid at reaction temperature and which are sufficiently good solvents for both catalyst and water at the reaction temperature for reductive hydrolysis to occur, are amenable to operation in the neat mode. Similarly, when the product alcohol is a good solvent for the starting nitrile, catalyst, and water, the product alcohol itself can be used as the solvent. Lower nitriles such as acetonitrile or propionitrile could thus use the product alcohol as the solvent. Adiponitrile and methylglutaronitrile, though not miscible with water at ambient temperature, become miscible at elevated temperatures, therefore, they can also be considered candidates for operation in the neat mode. Even nitriles which are not completely miscible with water are amenable to the neat mode provided they are capable of dissolving catalyst and sufficient water to favor reductive hydrolysis over simple hydrogenation.

The purpose of using a water immiscible solvent is to facilitate recovery and recycle of catalyst in the case where the product alcohol is water soluble. This mode is feasible when the nitrile or product alcohol is a sufficiently good solvent for both catalyst and water to favor reductive hydrolysis over simple hydrogenation to amine. The water-soluble product can be separated from the water-insoluble catalyst by simple decantation and/or extraction procedures.

Suitable water-immiscible solvents comprise aliphatic and aromatic hydrocarbons, and water immiscible ethers. Preferred solvents are toluene and t-butyl methyl ether.

The water-immiscible solvent mode is not applicable with hydrophobic nitriles, e.g., dodecanedinitrile or m-methyl benzyl cyanide, due to insufficient contact with water, resulting in hydrogenation to amine rather than reductive hydrolysis.

With hydrophobic nitriles such as dodecanedinitrile or α-methyl benzyl cyanide, a homogenizing solvent is required. This solvent need not be miscible with water, but must be capable of dissolving nitrile, catalyst, and sufficient water to favor reductive hydrolysis over hydrogenation. All the solvents described above for hydrogenation of nitriles to amines can be considered, but the preferred solvents are the lower boiling alcohols and ethers, for example, dimethoxyethane, p-dioxane, tetrahydrofuran (THP), 2-methoxyethanol, 2-ethoxyethanol (Cellosolve®), and 2-butoxyethanol (butyl cellosolve). THF is most preferred.

The amount of catalyst, excess tricyclohexylphosphine, temperature, agitation requirements and sources of hydrogen are the same as discussed above for hydrogenation of nitriles.

The pressure employed can be from about 100 kPa (1 atmosphere) to about 15000 kPa. Elevated pressures are preferred since the solubility of hydrogen is increased which leads to higher reaction rates. However, pressures above about 7000 kPa are generally avoided due to the high cost of equipment capable of operating at such pressures. The preferred pressure is in the range of about 700 kPa to about 7000 kPa.

The present invention further provides a selective reductive hydrolysis process wherein a dinitrile is partially hydrogenated to yield a hydroxynitrile using a ruthenium complex having the formula $Ru(\eta^3-C_6H_8-PCy_2)(PCy_3)Cl$ or $RuHCl(H_2)(PCy_3)_2$ as a catalyst. For example, the major intermediate in the reductive hydrolysis of adiponitrile, 6-hydroxycapronitrile, can be prepared in high yield if the reductive hydrolysis is stopped at an intermediate stage.

The dinitrile of the present process can be any aliphatic dinitrile comprising about 3 to about 19 carbon atoms, but preferably comprising about 6 to about 12 carbon atoms. Preferably, the carbon atoms are arranged in a linear or branched chain. Especially preferred examples of dinitriles are adiponitrile and dodecanedinitrile.

The amount of catalyst, excess tricyclohexylphosphine, temperature, solvents and modes of operation, amounts of water, pressure, agitation requirements and sources of hydrogen are the same as discussed above for the reductive hydrolysis of nitriles.

The desired product of the selective reductive hydrolysis, a hydroxynitrile, is an intermediate in one embodiment of the present redutive hydrolysis process which eventually results in the formation of a diol. The hydroxynitrile concentration in the reacting mixture passes through a maximum as the reaction progresses. One objective of this embodiment of the present invention is to maximize the concentration of the hydroxynitrile in the reacting mixture at the highest possible conversion of the starting nitrile. The yield of the hydroxynitrile and the position of the maximum with respect to dinitrile conversion depend on operating conditions such as temperature, hydrogen pressure, amount and kind of catalyst, dilution of starting dinitrile, as well as, the type of solvent. These variables in turn influence the optimum contact time for the reaction.

The optimum reaction time of the present invention needed to favor formation of a hydroxynitrile need be determined only once for any given set of reaction conditions. Once the optimum has been determined, it will remain constant as long as reaction conditions, such as catalyst, temperature, and pressure are held constant. The contact time in the present selective reductive hydrolysis process is therefore selected to favor yield of hydroxynitrile over yield of diol.

Complexes of the formula $Ru(\eta^3-C_6H_8-PCy_2)(PCy_3)Cl$ and $RuHCl(H_2)(PCy_3)_2$ are also useful as catalysts for reductive imination of nitriles to aldimines. For example, adiponitrile can be hydrogenated using $RuHCl(H_2)(PCy_3)_2$ in the presence of n-butylamine to produce 5-formylvaleronitrile butylimine and adipaldehyde dibutylimine as illustrated by the following equations.

The imine products are formed with greater than 95% selectivity at complete adiponitrile (ADN) conversion, with only traces of primary and secondary amine by-products. The advantages of using the ruthenium complexes of the present invention as catalysts are high reaction rate and high selectivity to aldimines.

A primary amine is a required reactant in the reductive imination reaction. The amine can be formed in situ (for example, by initial hydrogenation of nitrile) or can be added as a separate ingredient. At least one mole of amine is required for one mole of aldimine to form, but larger amounts, as much as 30 moles of amine per mole of nitrile or even more, can be used to increase the rate of reductive imination compared to simple hydrogenation, thus increasing the yield of aldimines compared to amines. Suitable primary amines comprise the compounds $RNH_2$, wherein R is an aliphatic, or alicycic or aromatic hydrocarbyl group, that is a linear, branched, or cyclic arrangement of carbon atoms connected by single, multiple, or aromatic bonds only, with hydrogens attached as appropriate. R can optionally be substituted with atoms or functional groups which do not interfere with the desired chemistry, such as hydroxy, ether, amide, ester, alkoxy or aryloxy groups. Examples of suitable primary amines include methylamine, ethylamine, n-propylamine, isopropylamine, n-butylamine, isobutylamine, tert-butylamine, cyclopentylamine, cyclohexylamine, benzylamine, and dine, and o-, m-, or p-toluidine. Preferred primary amines include n-butylamine, aminocapronitrile, hexamethylenediamine, 5-amino4-methyl-valeronitrile, 5-amino-2-methylvaleronitrile, 2-methyl- 1,5-diaminopentane, 12-aminododecanenitrile, and 1,12-diaminododecane.

The amount of catalyst, excess tricyclohexylphosphine, temperature, solvents, agitation requirements, and sources of hydrogen are as described above for hydrogenation of nitriles to amines. A preferred mode of operation is with use of the primary amine as reaction solvent. This provides for the highest possible ratio of amine to nitrile (about 25 to about 30 moles of amine per mole of nitrile, or more) and maximizes formation of the aldimine product compared to primary amine.

The key variable in determining whether a nitrile is hydrogenated to amine or reductively iminated has been found to be hydrogen pressure. As illustrated by the detailed examples of the present invention with the ruthenium complex having the formula $RuHCl(H_2)(PCy_3)_2$ as catalyst and n-butylamine as solvent, at 860 kPa $H_2$, ADN can be hydrogenated normally, via ACN, to HMD, while at 7000 kPa $H_2$, reductive imination can occur, forming 5-formylvaleronitrile butylimine and adipaldehyde dibutylimine.

One possible explanation for this dramatic change in selectivity is suggested by the ability of these ruthenium complexes to form dihydrogen complexes. Nitrile hydrogenation is thought to proceed by coordination of nitrile to catalyst followed by stepwise addition of two moles of hydrogen. After the first addition, it is thought that an intermediate imine complex is formed. Usually, addition of the second mole of dihydrogen is rapid, forming amine. However, if dihydrogen is able to displace the intermediate imine from the ruthenium complex catalyst, addition of the second mole of dihydrogen may be slowed significantly, allowing the intermediate imine to react with amines present in the mixture to form aldimines, as outlined below.

-continued aldimine

Higher hydrogen pressures increase the concentration of dihydrogen in solution, thereby increasing its ability to form complexes with the catalyst. It should be understood that this is only one possible explanation, and that it is not necessary to understand the exact mechanism by which aldimines are formed in order to successfully apply the present invention.

Pressure can range from about 1000 kPa to about 15000 kPa. Higher pressures can be used but are generally avoided due to the increased cost of equipment capable of operating at those pressures. Use of lower pressures can result in formation of amines rather than aldimines.

Preferably, the reductive imination process of the present invention occurs at a pressure of about 1825 kPa to about 7000 kPa.

Another embodiment of the present invention is a simple process for separation of the ruthenium complex catalyst from hydrogenation or reductive hydrolysis product compounds and recycle of the catalyst. Conventional methods of accomplishing such separations include fractional distillation, fractional crystallization, extraction, and chromatography. Distillation methods in particular are very commonly used, where, for example, hexamethylenediamine may be separated from the less volatile hydrogenation catalyst by fractional distillation, but the high temperature and sub-atmospheric pressure required, due to the relatively high boiling point of hexamethylenediamine, may adversely affect catalyst stability.

Unlike most homogeneous catalysts, the catalysts of the present invention are unexpectedly stable in the presence of water. Therefore, in cases where the product compounds are soluble in water, and where a reaction solvent is employed which is immiscible with water, the product compounds can be separated from the catalyst and reaction solvent by extraction with water. The catalyst is essentially insoluble in water and remains dissolved in the reaction solvent while the water-soluble product compounds are removed into the water extracts. The resulting solution of catalyst in the reaction solvent, which can be dried if desired, is then recycled. The product compounds can be recovered from the water extracts by distillation or any other desired method, without concern for catalyst stability.

Advantages of separation by water extraction comprise simplicity, mild conditions, and low energy consumption. In particular, the extraction can be conducted at mild temperatures, between about 20° C. and about 100° C., and mild pressures, between about 100 kPa and about 500 kPa, which are desirable from the standpoint of maintaining catalyst stability.

EXAMPLES

All manipulations were carded out in a Vacuum Atmospheres glove box (Vacuum Atmospheres Company, Hawthorne, Calif.) with continuous nitrogen purge. Reactions involving hydrogen at pressures of less than 860 kPa were carded out in a 50 mL Fischer-Porter tube. Higher pressure reactions involving hydrogen were carried out in a 50 mL Hastalloy C autoclave (Autclave Engineers, Erie, Pa.) stirred at 1500 rpm with a gas-inducing turbine blade agitator. Reactor loading and unloading was within the glovebox.

Hydrogenation products were analyzed by gas chromotography using a 0.53 mm internal diameter×30 m long DB-5 column from J&W Scientific, Folsom, Calif. Infrared spectra were obtained on a Nicolet 205 FTIR spectrometer. NMR spectra were obtained on a GE QE 300 (300 MHz $^1$H, 121 MHz $^{31}$P) spectrometer. Positive H and P shifts were reported as downfield from external TMS or $H_3PO_4$ respectively.

$(COD)RuCl_2$ was prepared according to the method disclosed by M. O. Albers et al., *Inorganic Syntheses*, 1989, 26, 68. Tricyclohexylphosphine is available from Strem Chemical Co., Newburyport, Mass. Trimethylsilylmethylmagnesium chloride, $(CH_3)_3SiCH_2MgCl$ and Aliquat 336® are available from Aldrich Chemical Co, Milwaukee, Wis. Petroleum ether, toluene and tetrahydrofuran was purified before use by distillation from sodium benzophenone.

| Abbreviations used throughout are | |
|---|---|
| ACN | aminocapronitrile |
| ADN | adiponitrile |
| COD | 1,5-cyclooctadiene |
| CPI | 2-cyano cyclopentylimine |
| Cy | cyclohexyl |
| DMF | N,N-dimethyl formamide |
| DNPOP | dinitrodiphenyl ether |
| Dytek A ® | 2-methyl-pentamethylene diamine |
| Et | ethyl |
| HMD | hexamethylenediamine |
| HMI | hexamethyleneimine (aka azacycloheptane) |
| kPa | kilo Pascals |
| Me | methyl |
| MGN | 2-methylglutaronitrile |
| MTBE | methyl t-butyl ether |
| Ph | phenyl |
| THA | tetrahydroazapine |
| THF | tetrahydrofuran |
| Definitions | |
| Yield: | moles of product formed/moles of reactant charged × 100% |
| Selectivity: | moles of product formed/moles of reactant consumed × 100% |

EXAMPLE 1

Preparation of Ru($\eta^3$-$C_6H_8$-$PCy_2$)($PCy_3$)Cl

A mixture of 4.0 g $(COD)RuCl_2$, 12.0 g tricyclohexylphosphine and 200 mL THF was stirred for 15 minutes. Then, 16 mL $Me_3SiCH_2MgCl$ (1M in $Et_2O$,) was added over approximately 2 minutes. The resulting mixture was stirred for 16 h at 20° C. The THF was then removed, in vacuo, to dryness. The residue was extracted twice with 50 mL portions of toluene, and the extracts were filtered through a medium porosity fritted-glass funnel. The toluene was removed, in vacuo, to dryness, and the dark red-purple semisolid product was stirred with petroleum ether to give a powdery solid, which was collected by filtration and dried in vacuo. Yield 6.25 g.

Gas chromatographic analysis of the volatile products recovered from a Ru($\eta^3$-$C_6H_8$-$PCy_2$)($PCy_3$)Cl preparation showed the presence of cyclooctene and tetramethylsilane.

An analytical sample of Ru($\eta^3$-$C_6H_8$-$PCy_2$)($PCy_3$)Cl was recrystallized by dissolving 0.2 g crude Ru($\eta^3$-$C_6H_8$-$PCy_2$)($PCy_3$)Cl in 4 g boiling 1,2-dimethoxyethane, rapidly filtering while hot (syringe filter), and slow cooling. The supernatant was decanted and the crystals washed twice with small portions of diethylether, then dried briefly in vacuo. The dark purple crystals were individual, well-formed needles, but an attempt to obtain an x-ray crystal structure showed them to be twinned. Elemental analysis Found: C 60.78, 61.21, H 8.84, 9.10, P 8.26, 8.61, Cl 5.38, 4.2. Calculated for $RuC_{36}H_{63}P_2Cl$: C 62.27 H 9.15 P 8.92, Cl 5.11. The mole ratios of elements calculated from the analysis were C: 35.6, H: 63.0, P: 1.9, Cl: 0.8 and were consistent with that expected based on the molecular formula (C: 36, H: 63, P: 2, Cl: 1). Further, NMR confirmed the number of C, H, and P atoms present.

Cryoscopic molecular weight, in benzene, showed the complex to be monomeric and agreed with the proposed structure: Found 678, Calculated 694.

EXAMPLE 2

Adiponitrile Hydrogenation using $Ru(\eta^3-C_6H_8-PCy_2)(PCy_3)Cl$ as catalyst A mixture of 0.055 g crude $Ru(\eta^3-C_6H_8-PCy_2)(PCy_3)Cl$ (0.08 mmol), 0.067 g adiponitrile (ADN) (0.62 mmol) and 0.064 g aminocapronitrile (0.57 mmol) in 35 mL toluene was pressured with hydrogen to 860 kPa and heated to 60° C. After 6 hours, all of the adiponitrile had been hydrogenated and the composition as determined by gas chromatography, was 60% hexamethylenediamine (HMD) and 40% aminocapronitrile. Aminocapronitrile is the main intermediate when ADN is hydrogenated to HMD, therefore this experiment demonstrated the hydrogenation of aminocapronitrile to HMD.

EXAMPLE 3

Preparation of $RuHCl(H_2)(PCy_3)_2$ from $Ru(\eta^3-C_6H_8-PCy_2)(PCy_3)Cl$ A mixture of 0.3 g crude $Ru(\eta^3-C_6H_8-PCy_2)(PCy_3)Cl$ (0.432 mmol) and 10 mL petroleum ether was treated with 930 kPa $H_2$ for 3 hours at 20° C. The yellow-orange precipitate was collected by filtration and rinsed with cold petroleum ether, then dried under nitrogen (yield 0.0734 g, 0.104 mmol, 24%).

EXAMPLE 4

Alternate Preparation of $RuHCl(H_2)(PCy_3)_2$ from $Ru(\eta^3-C_6H_8-PCy_2)(PCy_3)Cl$ A deep purple solution of 1.08 mmol $Ru(\eta^3-C_6H_8-PCy_2)(PCy_3)Cl$ in ~15 mL petroleum ether was treated with 860 kPa $H_2$ for 22 hours. The resulting yellow, powdery precipitate was collected by filtration, rinsed with a small amount of cold petroleum ether, and dried under $N_2$ to give 0.6764 g $RuHCl(H_2)(PCy_3)_2$ (0.97 mmol, 90% yield).

EXAMPLE 5

ADN Hydrogenation using $RuHCl(H_2)(PCy_3)_2$ as catalyst

A solution of 0.069 g $RuHCl(H_2)(PCy_3)_2$ (0.1 mmol) and 0.59 g adiponitrile (5.5 mmol) in 35 mL n-butyl amine was charged to a Fisher-Porter tube, pressurized to 860 kPa with $H_2$, and heated to 80° C. Samples were withdrawn periodically and analyzed by gas chromotography to follow the course of the reaction. The ADN was smoothly hydrogenated, via aminocapronitrile (ACN) as intermediate, to hexamethylenediamine. After 8.3 hours, the hydrogenation was complete (all ADN and ACN consumed) and the yield of HMD was 89%.

EXAMPLE 6

Preparation of $RuH_2(H_2)_2(PCy_3)_2$ from $Ru(\eta^3-C_6H_8-PCy_2)(PCy_3)Cl$ or from $RuHCl(H_2)(PCy_3)_2$ Since $Ru(\eta^3-C_6H_8-PCy_2)(PCy_3)Cl$ was found to rapidly convert to $RuHCl(H_2)(PCy_3)_2$ upon exposure to hydrogen, either one can be used as starting material for the preparation of $RuH_2(H_2)_2(PCy_3)_2$.

EXAMPLE 6A

Preparation of $RuH_2(H_2)_2(PCy_3)_2$ from $Ru(\eta^3-C_6H_8-PCy_2)(PCy_3)Cl$ A mixture of 0.2614 g $Ru(\eta^3-C_6H_8-PCy_2)(PCy_3)Cl$, 15 mL benzene, and 0.0378 g benzyl triethylammonium chloride (as phase-transfer catalyst) was placed in a 50 cc Fisher-Porter tube and 1 mL of 50% aqueous NaOH was added by syringe under a counterstream of hydrogen. The mixture was pressured to 860 kPa $H_2$ and stirred for 22.3 hours. Phosphorus nmr showed a singlet at 79 ppm and proton nmr showed a hydride at −7.9 ppm, indicating the major product to be $RuH_2(H_2)_2(PCy_3)_2$.

EXAMPLE 6B

Preparation of $RuH_2(H_2)_2(PCy_3)_2$ from $RuHCl(H_2)(PCy_3)_2$

A Fisher-Porter tube was charged with 0.7 g $RuHCl(H_2)(PCy_3)_2$ (1.0 mmol), 25 mL toluene, and 1 drop of Aliquat 336®. Under a counterstream of hydrogen, 1 mL of 50% aqueous NaOH was added. The tube was pressurized to 860 kPa with hydrogen and stirred for 19.5 hours. The hydrogen was vented and the reaction brought into the glovebox, where the pale yellow toluene phase was separated from the milky white aqueous phase. The organic phase was washed with water to remove any residual caustic. The major component as determined by $^{31}P$ nmr, was $RuH_2(H_2)_2(PCy_3)_2$.

EXAMPLE 7

Selective hydrogenation of ADN to ACN using $RuHCl(H_2)(PCy_3)_2$ in n-butylamine and complete hydrogenation to HMD A mixture of 0.1 mmol $RuHCl(H_2)(PCy_3)_2$ and 5.1 mmol ADN in 35 mL n-butylamine was heated in a Fisher-Porter tube at 60° C. under 860 kPa $H_2$. After 2.3 h, the ADN conversion was 96% and the ACN selectivity was 61%, vs 32% expected statistically at that conversion (see FIG. 1). The hydrogenation was continued, and after 4.5 hours, the ADN conversion was 100% and the yield of HMD was 90%.

EXAMPLE 8

ADN hydrogenation using $RuHCl(H_2)(PCy_3)_2$ in n-amylamine

A mixture of 0.106 mmol $RuHCl(H_2)(PCy_3)_2$ and 6.46 mmol ADN, and 0.244 mmol $PCy_3$ in 35 mL n-amylamine was heated in a Fisher-Porter tube at 80° C. under 860 kPa $H_2$. After 6.0 hours, ADN conversion was complete and the yield of HMD was 97%.

EXAMPLE 9

Dodecanedinitrile hydrogenation in toluene/water using RuHCl(H$_2$)PCy$_3$)$_2$ A mixture of 0.059 mmol RuHCl(H$_2$)(PCy$_3$)$_2$, 2.87 mmol dodecanedinitrile, 5 mL water and 35 mL toluene was stirred in a Fisher-Porter tube at 80° C. under 860 kPa H$_2$. After 22 hours, gc analysis showed that the dinitrile was completely converted and the product, 1,12-dodecanediamine, formed in 85% yield.

EXAMPLE 10

Hydrogenation of α-methyl benzyl cyanide in toluene/H$_2$O

A mixture of 0.0761 mmol RuHCl(H$_2$)(PCy$_3$)$_2$, 8.1 mmol α-methyl benzyl cyanide, 0.11 g cyclododecane (g.c. internal standard), 5 mL water, and 30 mL toluene was stirred in an autoclave and heated to 80° C. under 7000 kPa H$_2$. After 4.1 hours, gc analysis showed 1% unreacted nitrile, 9% 2-phenylpropanol and 89% 2-phenylpropylamine.

COMPARATIVE EXAMPLE A

Comparison ADN hydrogenation using RuHCl(PPh$_3$)$_3$

A mixture of 0.02 mmol RuHCl(PPh$_3$)$_3$ and 0.32 mmol ADN in 30 mL toluene was heated in a Fisher-Porter tube to 80° C. under 860 kPa H$_2$. After 2 hours, gc analysis showed that no hydrogenation had occurred. The mixture was heated under 860 kPa H$_2$ to 135° C. overnight. GC analysis showed that no hydrogenation had occurred.

EXAMPLE 11

ADN reductive hydrolysis using RuHCl(H$_2$)(PCy$_3$)$_2$ in THF

A mixture of 0.1068 mmol RuHCl(H$_2$)(PCy$_3$)$_2$, 5.43 mmol ADN, 16.9 g water and 17.7 g THF was stirred in an autoclave at 80° C. under 7000 kPa H$_2$. After 2.5 hours, gc analysis using an internal standard method showed that all the ADN had been consumed and the yield of 1,6-hexanediol was 95%. No ACN or HMD was detected. The remaining 5% of the ADN was accounted for as hexamethyleneimine (HMI). Mass balance was excellent, indicating that no significant nitrile hydrolysis to amides, acids, or esters occurred.

EXAMPLE 12

ADN reductive hydrolysis using RuHCl(H$_2$)(PCy$_3$)$_2$ in toluene

A mixture of 0.1 mmol RuHCl(H$_2$)(PCy$_3$)$_2$, 5.35 mmol ADN, 5 g water and 35 mL toluene was stirred in an autoclave at 80° C. under 7000 kPa H$_2$. After 5.5 hours, gc analysis showed that all the ADN had been converted to a mixture of 84% hexanediol and 16% aminohexanol.

EXAMPLE 13

MGN reductive hydrolysis using RuHCl(H$_2$)(PCy$_3$)$_2$

A mixture of 0.1 mmol catalyst, 5.43 mmol MGN, 17.7 g THF, 16.3 g water, and 0.1435 g cyclododecane (internal standard for gc analysis) was stirred in an autoclave and heated to 80° C. under 7000 kPa H$_2$. After 1 hour, the MGN conversion was 96% and the selectivity to hydroxynitrile was 88%. After 4 hours, the MGN was completely converted and the yield of 2-methylpentanediol was 90%.

EXAMPLE 14

Glutaronitrile reductive hydrolysis using RuHCl(H$_2$)(PCy$_3$)$_2$

A mixture of 0.1 mmol RuHCl(H$_2$)(PCy$_3$)$_2$, 5.26 mmol glutaronitrile, 5 g water and 35 mL toluene was stirred in an autoclave at 80° C. under 7000 kPa H$_2$. After 7.6 hours, gc analysis showed that the glutaronitrile conversion was 99% and the yield of 1,5-pentanediol was 89%.

EXAMPLE 15

Dodecanedinitrile reductive hydrolysis in THF/water using RuHCl(H$_2$)(PCy$_3$)$_2$ A mixture of 0.066 mmol RuHCl(H$_2$)(PCy$_3$)$_2$, 2.95 mmol dodecanedinitrile, 15 mL water and 20 mL THF was stirred in a Fisher-Porter tube at 80° C. under 860 kPa H$_2$. After 22.1 hours, gc analysis showed that the dinitrile conversion was 97% and the yield of 1,12-dodecanediol was 78%. Most of the remaining dinitrile (17%) was accounted for as 12-hydroxydodecanenitrile, the half-reductively-hydrolyzed intermediate, suggesting that the ultimate yield of diol would have been higher at longer reaction time.

EXAMPLE 16

Reductive hydrolysis of methyl 3-cyano-isobutyrate

A mixture of 0.05 mmol RuHCl(H$_2$)(PCy$_3$)$_2$, 0.54 mmol methyl-3-cyanoisobutyrate (prepared by addition of HCN to methyl methacrylate), 17.7 g THF, 15.3 g water, and 0.0596 g cyclododecane (internal standard for gc analysis) was stirred in an autoclave and heated to 100° C. under 7000 kPa H$_2$. After 3.2 hours, the nitrile was completely and cleanly converted to methyl-butyrolactone, which formed by trans-esterification/cyclization of the intermediate hydroxyester, methyl 2-methyl-4-hydroxybutyrate.

EXAMPLE 17

Reductive hydrolysis of α-methyl benzyl cyanide in THF

A mixture of 0.0761 mmol RuHCl(H$_2$)(PCy$_3$)$_2$, 7.8 mmol α-methyl benzyl cyanide, 15 mL water, and 20 mL THF was stirred in an autoclave and heated to 80° C. under 7000 kPa H$_2$. After 5.6 hours, gc/ms analysis showed that the nitrile was completely converted to a mixture of 79% 2-phenylpropanol and 21% 2-phenylpropylamine.

EXAMPLE 18

Reductive hydrolysis of optically active 2-(α-cyanoethyl)-6-methoxynaphthalene using RuHCl(H$_2$)(PCy$_3$)$_2$ Note that the nitrile used in this example was a chiral substrate, initially with 73% enantiomeric excess (ee). A mixture of 0.0521 mmol RuHCl(H$_2$)(PCy$_3$)$_2$, 0.53 mmol nitrile, 15 mL water, and 20 mL THF was stirred in an autoclave and heated to 60° C. under kPa H$_2$. After 6.2 hours, gc analysis showed the yield of alcohol to be about 50%. Analysis of the alcohol (isolated by thin layer chromatography and identified by nmr) by liquid chromatography on a chiral column showed it to be about 35% ee.

COMPARATIVE EXAMPLE B

Attempted Reductive hydrolysis of ADN using Raney Ni

A mixture of 0.2 g water-wet Cr-promoted Raney Ni (W. R. Grace's "2400", Baltimore, Md.), 0.60 g ADN, 30 mL water, and 5 mL toluene was heated to 80° C. in a Fisher-Porter tube under 860 kPa H$_2$. After 8.1 h, the ADN was completely consumed. The main products were ACN, HMD, and HMI. No hexanediol was detected.

COMPARATIVE EXAMPLE C

Attempted Reductive hydrolysis of ADN using a palladium on carbon catalyst (Pd/C)

A mixture of 5 mmol ADN, 1.1 g 0.5% Pd/C, 15 g water and 17 g toluene was heated to 120° C. in a Fisher-Porter tube pressurized to 860 kPa with hydrogen. After 6.3 h, gc analysis showed that 96% of the ADN had been converted. The major product was tris(5-cyanopentyl)amine (about 58%) with lesser amounts of di(5-cyanopentyl)amine (14%) and 5-cyanopentyl HMI (14%). Only a trace of ACN was observed. No significant amount of alcohol was formed.

COMPARATIVE EXAMPLE D

Attempted Reductive hydrolysis of ADN using a Rh/MgO Catalyst

A sample of Rh/MgO was prepared according to the procedure described by F. Mares et al., J. Catal.,112, 145 (1988), and in U.S. Pat. No. 4,389,348 (1983), and U.S. Pat. No. 4,601,859 (1986). A mixture of 0.25 g of the Rh catalyst, 0.58 g ADN, 15 mL water and 20 mL THF was stirred and heated in a Fisher-Porter tube at 80° C. under 860 kPa H$_2$. After 3.8 hours, gc analysis showed 82% ADN, 5% ACN, and 1% hydroxycapronitrile, as well as other products. The low conversion showed the relatively low activity of this catalyst, and the 5:1 ratio of ACN:hydroxynitrile clearly showed that hydrogenation predominated over reductive hydrolysis.

EXAMPLE 19

Selective hydrogenation of ADN to 5-formylvaleronitrile butylimine and adipaldehyde dibutylimine A solution of 0.1 mmol RuHCl(H$_2$)(PCy$_3$)$_2$, 0.24 mmol PCy$_3$, and 5.36 mmol ADN in 35 mL n-butylamine was heated in a stirred autoclave at 60° C. under 7000 kPa H$_2$. After 1 h, gc analysis showed that the ADN conversion was about 84%. However, only 2% of the ADN was converted to ACN. The remaining ADN was accounted for as 5-formylvaleronitrile butylimine (84% selectivity, 71% yield) and adipaldehyde dibutylimine (13% selectivity, 11% yield). The products were identified by gc/ms, and 5-formylvaleronitrile butylimine was also synthesized from 5-formylvaleronitrile and butylamine to confirm the gc/ms and gc retention time.

Allowing the hydrogenation to continue resulted in further conversion of the intermediate 5-formylvaleronitrile butylimine to adipaldehyde dibutylimine. After 7 h, the composition was <1% ADN, 9% 5-formylvaleronitrile butylimine, and 90% adipaldehyde dibutylimine.

A series of experiments with similar composition to the one immediately above but with varying hydrogen pressure was carried out to determine the effect of pressure on product selectivity in hydrogenations using RuHCl(H$_2$)(PCy$_3$)$_2$. All runs used 0.1 mmol RuHCl(H$_2$)(PCy$_3$)$_2$, 0.2 mmol extra PCy$_3$, and 5-6 mmol ADN in 35 mL n-butylamine solvent. Hydrogenations were conducted at 60° C. for 7 hours and the products were analyzed by GC, with the results shown in the table below. In this case, primary mines were produced at pressures of less than about 350 kPa, preferably at or below about 1825 kPa, most preferably at or below about 790 kPa. Aldimines were produced at higher pressures of about 1825 kPa to about 7000 kPa, preferably at or above about 3550 kPa, most preferaby at or above about 7000 kPa. At intermediate pressures where the above ranges overlap, mixtures of amines and aldimines were obtained.

TABLE

| Hydrogen Pressure (kPa) | Normal primary amines (ACN + HMD) | Aldimines (5-formylvalero-nitrile butylimine and adipaldehyde dibutylimine) | Others |
|---|---|---|---|
| 790 | 94% | 0% | 6% (THA + HMI) |
| 1825 | 75% | 25% | |
| 3550 | 10% | 90% | |
| 7000 | 0% | 99% | 1% |

EXAMPLE 20

Hydrogenation of 4,4'-dinitrodiphenylether (DNPOP) using RuHCl(H$_2$)(PCy$_3$)$_2$ A mixture of 0.04 mmol RuHCl(H$_2$)(PCy$_3$)$_2$ and 0.4 mmol DNPOP in 35 mL toluene was heated in a Fisher-Porter tube at 60° C. under 860 kPa H$_2$. After 3 hours, the composition was 2% DNPOP, 91% 4-amino-4'-nitrodiphenylether, and 7% oxydianiline. Selectivity to the amino-nitro intermediate was 93% at 98% DNPOP conversion. After 22.3 hours, all of the DNPOP had been converted, and the products consisted of 33% 4-amino-4'-nitrodiphenylether and 67% oxydianiline.

EXAMPLE 21

Nitrobenzene hydrogenation using RuHCl(H$_2$)(PCy$_3$)$_2$

A solution of 0.1 mmol RuHCl(H$_2$)(PCy$_3$)$_2$ and 1 mL nitrobenzene in 35 mL toluene was heated in a Fisher-Porter tube to 60° C. under 860 kPa H$_2$. After 6 hours, 25% of the nitrobenzene had been converted cleanly to aniline.

What is claimed is:

1. A ruthenium complex having the formula $Ru(\eta^3\text{-}C_6H_8\text{-}PCy_2)(PCy_3)Cl$, wherein Cy is a cyclohexyl group.

2. A process for the preparation of a ruthenium complex having the formula $Ru(\eta^3\text{-}C_6H_8\text{-}PCy_2)(PCy_3)Cl$, wherein Cy is a cyclohexyl group, comprising: (a) contacting a ruthenium compound of the formula $R^1{}_2RuX_2$, wherein $R^1$ is a mono- or poly-, cyclic- or acyclic alkene ligand, present as either two separate ligands or as a single polyalkene ligand and X is a halide or a pseudohalogen; with tricyclohexylphosphine in the presence of a solvent; (b) adding a base to the solution; and (c) isolating the ruthenium complex from the solution.

3. The process of claim 2 wherein the ruthenium compound is selected from the group consisting of: (norbornadiene)$RuCl_2$, (cyclohexadiene)$RuCl_2$, (cycloheptatriene)$RuCl_2$, and (1,5-cyclooctadiene)$RuCl_2$.

4. The process of claim 3 wherein the ruthenium compound is (1,5-cyclooctadiene)$RuCl_2$.

5. The process of claim 2 wherein contact is made in the presence of an aprotic solvent at a temperature of about $-78°$ C. to about 200° C. under an inert atmosphere with the base having a $pK_a$ greater than 13.

6. A process for the preparation of a ruthenium complex having the formula $RuHCl(H_2)(PCy_3)_2$, wherein Cy is a cyclohexyl group, comprising the steps of:

(a) contacting a ruthenium complex having the formula $Ru(\eta^3\text{-}C_6H_8\text{-}PCy_2)(PCy_3)Cl$ wherein Cy is a cyclohexyl group with gaseous hydrogen in the presence of a solvent to form a solution or suspension; and (b) agitating the solution or suspension to form the ruthenium complex having the formula $RuHCl(H_2)(PCy_3)_2$.

7. The process of claim 6 wherein contact is made at a temperature of about $-80°$ C. to about 200° C.

8. The process of claim 6 wherein the solvent is selected from the group consisting of: aromatic hydrocarbons, aliphatic hydrocarbons, ethers and amines.

9. The process of claim 8 wherein the solvent is an aliphatic hydrocarbon.

10. The process of claim 6 wherein the solution or suspension further comprises an amine base.

11. A process for the preparation of a ruthenium complex having the formula $RuH_2(H_2)_2(PCy_3)_2$, wherein Cy is a cyclohexyl group, comprising the steps of:

(a) contacting a ruthenium complex having the formula $Ru(\eta^3\text{-}C_6H_8\text{-}PCy_2)(PCy_3)Cl$ or $RuHCl(H_2)(PCy_3)_2$ wherein Cy is a cyclohexyl group with gaseous hydrogen in the presence of water, a strong base, an organic solvent and a phase transfer catalyst to form a biphasic medium; and (b) agitating the medium to form the ruthenium complex having the formula $RuH_2(H_2)_2(PCy_3)_2$.

12. The process of claim 11 wherein the phase transfer catalyst is selected from the group consisting of: quaternary ammonium halides, linear or cyclic polyethers and linear or cyclic polyether amines.

13. The process of claim 12 wherein the base is sodium hydroxide, the solvent is a polar aprotic solvent, and contact is made at a temperature of about $-30°$ C. to about 200° C. at a pressure between about 100 kPa and about 15000 kPa.

14. The process of claim 13 wherein the phase transfer catalyst is benzyltriethylammonium chloride and the solvent is benzene or toluene.

* * * * *